(12) United States Patent
Yadav

(10) Patent No.: US 10,035,144 B2
(45) Date of Patent: Jul. 31, 2018

(54) MULTI-ACID POLYMERS AND METHODS OF MAKING THE SAME

(71) Applicant: Nissan North America, Inc., Franklin, TN (US)

(72) Inventor: Rameshwar Yadav, Novi, MI (US)

(73) Assignee: Nissan North America, Inc., Franklin, TN (US)

( * ) Notice: Subject to any disclaimer, the term of this patent is extended or adjusted under 35 U.S.C. 154(b) by 0 days.

(21) Appl. No.: 15/591,682

(22) Filed: May 10, 2017

(65) Prior Publication Data

US 2017/0274369 A1 Sep. 28, 2017

Related U.S. Application Data

(62) Division of application No. 15/078,374, filed on Mar. 23, 2016, now Pat. No. 9,694,357.

(51) Int. Cl.

| | |
|---|---|
| *B01J 39/20* | (2006.01) |
| *C07C 311/09* | (2006.01) |
| *C08F 8/36* | (2006.01) |
| *C08F 8/40* | (2006.01) |
| *B01J 39/05* | (2017.01) |
| *C08J 5/22* | (2006.01) |
| *C07F 9/38* | (2006.01) |
| *H01M 8/0239* | (2016.01) |

(52) U.S. Cl.
CPC ............ *B01J 39/20* (2013.01); *B01J 39/05* (2017.01); *C07C 311/09* (2013.01); *C07F 9/3873* (2013.01); *C08F 8/36* (2013.01); *C08F 8/40* (2013.01); *C08J 5/225* (2013.01); *H01M 8/0239* (2013.01); *C08J 2327/22* (2013.01); *C08J 2329/10* (2013.01); *C08J 2341/00* (2013.01); *H01M 2250/20* (2013.01)

(58) Field of Classification Search
CPC ......... B01J 39/20; B01J 39/05; C07C 311/09; C08F 8/36; C08F 8/40; C08J 5/225; C08J 2339/10; C08J 2327/22; C08J 2341/00; C07F 9/3873; H01M 8/0239; H01M 2250/20
USPC ........................................................ 521/27
See application file for complete search history.

(56) References Cited

U.S. PATENT DOCUMENTS

| | | | |
|---|---|---|---|
| 3,941,834 A | 3/1976 | Lee | |
| 5,422,411 A | 6/1995 | Wei et al. | |
| 6,090,895 A | 7/2000 | Mao et al. | |
| 2002/0160272 A1 | 10/2002 | Tanaka et al. | |
| 2011/0195341 A1 | 8/2011 | Katayama | |
| 2011/0318671 A1* | 12/2011 | Uensal ............... | B01D 67/0006 429/492 |
| 2014/0011129 A1* | 1/2014 | Murai .................... | C07C 233/81 430/108.22 |

FOREIGN PATENT DOCUMENTS

WO 2012133871 A1 10/2012

OTHER PUBLICATIONS

Thomas et al. "Self-emulsifying polymerization (SEP of 3,6-dioxa-Δ-4-trifluoromethyl perfluorooctyl trifluoromethyl sulfonamide with tetrafluoroethylene", J. of Fluorine Chemistry, 126 (2005), 1057-1064, www.sciencedirectxom.*
Schaberg et al. "New Multi Acid Side-Chain Ionomers for Proton Exchange Membrane Fuel Cells", 3M Company, ECS Transactions, 33 (I) 627-633 (2010).*
Thomas et al. "Self-emulsifying polymerization (SEP of 3,6-dioxa-Δ-4-trifluoromethyl perfluorooctyl trifluoromethyl sulfonamide with tetrafluoroethylene", J. of Fiuorine Chemistry, 126 (2005), 1057-1064, www.sciencedirectxom.*
Nworie Chimaroke "Synthesis of a 4-(Trifluoromethyl)-2-Diazonium Perfluoroalkyl Benzenesuflonylimide (PFSI) Zwitterionic Monomer for Proton Exchange Membrane Fuel Cell", School of graduate Studies, East Tennessee State University, 2014.*
Schaberg et al. "New Multi Acid Side-Chain Ionomers for Proton Exchange Membrane Fuel Cells", 3M Company, ECS Transactions, 33 (1) 627-633 (2010).*
Yandrasits, Michael A., et al., "Membranes for PEM Fuel Cells", ACS Symposium Series; American Chemical Society; Washington, DC, 2010.
Zhang, Y.M., et al., "Development of Covalently Cross-linked and Composite Perfluorosulfonic Acid Membranes", ECS Transaction, 25(1), 1469-1472 (2009).
Hamrock, S., et al., "New Fluorinated Ionomers and Membranes for PEM Fuel Cells", Fuel Cell Seminar, Orlando, Florida, 2011.
Schaberg, M. S., et al., "New Multi Acid-Chain Ionomers for Proton Exchange Membrane Fuel Cells", ECS Transactions, 33(1), 627-633, 2010.
Nworie, Chimaroke, "Synthesis of a 4-(Trifluoromethyl)-2-Diazonium Perfluoroalkyl Benzenesuflonylimide (PFSI) Zwitterionic Monomer for Proton Exchange Membrane Fuel Cell",Electronic Theses and Dissertations, School of Graduate Studies East Tennessee State University, Johnson City, TN, May 2014.

(Continued)

*Primary Examiner* — Michael M Bernshteyn
(74) *Attorney, Agent, or Firm* — Young Basile Hanlon & MacFarlane, P.C.

(57) ABSTRACT

Multi-acid polymers for use as a fuel cell membrane, for example, have multi-acid monomers that have an imide base and more than two proton conducting groups. The multi-acid polymers are made by reacting a polymer precursor in sulfonyl fluoride or sulfonyl chloride form with a compound with an acid giving group. One example of a multi-acid polymer is:

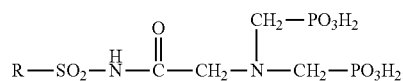

wherein R is one or more units of a non-$SO_2F$ or non-$SO_2Cl$ portion of a polymer precursor in sulfonyl fluoride or sulfonyl chloride form.

14 Claims, 3 Drawing Sheets

(56) References Cited

OTHER PUBLICATIONS

Zhang, Yunfeng et al., "Fabrication of a proton exchange membrane via blended sulfonimide functionalized polyamide", J Mater Sci (2014), 49:3442-3450.

Thomas H., Brian, et al., "Self-emulsifying polymerization (SEP) of 3,6-dioxa-D7-4-trifluoromethyl perfluorooctyl trifluoromethyl sulfonimide with tetrafluoroethylene", Journal of Fluorine Chemistry, 2005, pp. 1057-1064, vol. 126.

* cited by examiner

MULTI-ACID POLYMERS AND METHODS OF MAKING THE SAME

CROSS-REFERENCE TO RELATED APPLICATION

This application is a divisional of U.S. patent application Ser. No. 15/078,374, filed on Mar. 23, 2016, now U.S. Pat. No. 9,694,357, the entirety of which is incorporated herein by reference.

TECHNICAL FIELD

This disclosure relates to multi-acid polymers from multifunctional amino acids and sulfonyl halide precursors and methods of making the multi-acid polymers.

BACKGROUND

Proton exchange membrane fuel cells (PEMFCs) generate power from electrochemical conversion of fuels, such as hydrogen and hydrocarbons, at their anodes and oxidants, such as oxygen and air, at their cathodes using the polymer membrane as electrolyte. The membrane acts both as a proton conductor from anode to cathode and a barrier between fuels and oxidants. Current state-of-art membranes such as Nafion™ membranes, Aquivion™ membranes, and low equivalent weight (EW) perfluorosulfonic acid (PFSA) membranes have only one sulfonic acid group in the side chain. As a result, these membranes hold little water at any given relative humidity (RH %) and have very low ionic conductivity, especially at low RH % and at temperatures below 100° C.

SUMMARY

Disclosed herein are multi-acid polymers and multi-acid membranes, and methods of making the multi-acid polymers and multi-acid membranes.

A method of making the multi-acid polymers comprises reacting a polymer precursor in sulfonyl fluoride or sulfonyl chloride form with anhydrous ammonia to obtain a sulfonamide, wherein the polymer precursor in sulfonyl fluoride or sulfonyl chloride form has a formula R—$SO_2F$ or R—$SO_2Cl$, respectively, with R being one of more units of the polymer precursor without sulfonyl fluoride or sulfonyl chloride, and wherein the sulfonamide has a formula R—$SO_2$—$NH_2$. The sulfonamide is reacted with a compound of a formula COOH—X-AGG under a mild base condition, wherein X is one of $C_6H_3$ or $N(CH_2)_3$ and AGG is an acid giving group, to form the multi-acid polymer having an imide base and more than two proton conducting groups.

A multi-acid polymer disclosed herein has a multi-acid monomer with the following formula

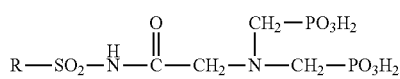

wherein R is one or more units of a non-$SO_2F$ or non-$SO_2Cl$ portion of a polymer precursor in sulfonyl fluoride or sulfonyl chloride form.

Another multi-acid polymer disclosed herein has a multi-acid monomer with the following formula:

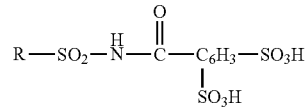

wherein R is one or more units of a non-$SO_2F$ or non-$SO_2Cl$ portion of a polymer precursor in sulfonyl fluoride or sulfonyl chloride form.

These and other aspects of the present disclosure are disclosed in the following detailed description of the embodiments, the appended claims and the accompanying figures.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
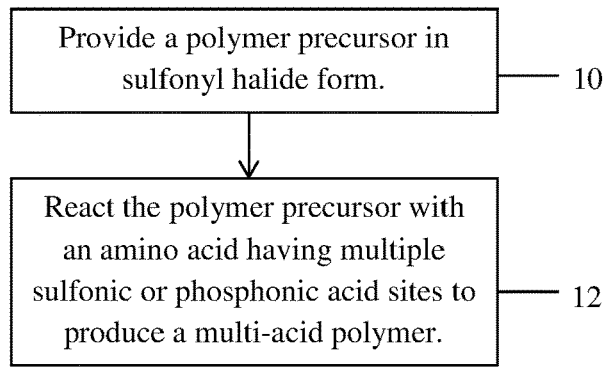
FIG. 1 is a flow diagram of a method of making a multi-acid polymer as disclosed herein.

Membranes that incorporate more acid groups for high ionic conductivity, especially at low RH % and at typical PEMFCs operating temperature, will enable simplified humidification systems, will improve performance of the fuel cell, and will reduce the cost for early commercialization of PEMFC electric vehicles. The multi-acid polymers disclosed herein, having two or more proton conducting sites, provide such membranes.

Ionic conductivity of membranes at low RH % is improved by increasing the acid groups in the membrane, such as sulfonic acids (—$SO_3H$ group), imide acids ($SO_2$—NH—$SO_2$ group), and phosphonic acids (—$PO_3H_2$ group). Increasing the acid groups reduces the equivalent weight (EW) because EW is inversely proportional to acid quantity in the membrane. However, increasing the acid groups by more than one in the side group in the current state-of-the-art membranes has been extremely difficult and challenging. The current membranes in the precursor form ($SO_2F$) have only one $SO_2F$ group that is hydrolyzed and ion-exchanged to accomplish only one $SO_3H$ group per side chain. Since, only one $SO_3H$ acid group per side chain is attained in the current membranes, the water uptake, ionic conductivity, IV performance, and power density are limited in such membranes that have applications in hydrogen and hydrocarbon PEMFCs. Additionally, because of limits on reactivity of typical starting monomers and comonomers, such as tetrafluoroethylene ($CF_2$=$CF_2$) monomer and Perfluoro (3-oxapent-4-ene) sulfonyl fluoride and Perfluoro (4-methyl-3,6-dioxaoct-7-ene)sulfonyl fluoride, increasing the acid group or reducing the EW below certain values, such as EW 1100, EW 870, EW 725, is difficult and expensive. Current state-of-the-art PFSA membranes that have just one sulfonic acid group are already expensive. Modifying such PFSA membranes to incorporate multi-acid groups currently requires sophisticated equipment and extremely high reaction conditions.

Currently, monomers having multiple acids or capable of holding multiple acids are non-existent for application in PEMFC membranes. In the PEMFC industry, it has been very challenging to develop membranes having phosphonic acid. Attempts to develop membranes with phosphonic acids for high temperature PEMFCs have been unsuccessful. Doping methods have been used to add phosphonic acids into the membrane; however, the phosphonic acids can leach from the membranes. The methods disclosed herein incorporate amino phosphonic acids into a polymer matrix, covalently attaching phosphonic acid to the polymer to produce a robust and stable membrane.

Multi-acids in the side group enable higher water uptake, higher ionic conductivity and higher power density in PEMFCs. The methods disclosed herein produce such multi-acid membranes. Some methods link various amino acids having multiple sulfonic acids or phosphonic acids with monomers, copolymers or polymers in sulfonyl fluoride or sulfonyl chloride ($SO_2F/Cl$) form to produce polymer electrolyte membranes or materials with high acid content for application in PEMFCs. An amino acid with more than one acid group is linked with a monomer, copolymer or polymer in $SO_2F/Cl$ form to produce multi-acid membranes. Methods disclosed herein use amino acid compounds that have a primary amine group ($-NH_2$) attached to multiple sulfonic acids or phosphonic acids. The methods incorporate varieties of amino sulfonic acids or amino phosphonic acids or amino sulfonyl halides that are highly acidic.

Embodiments of the multi-acid membranes disclosed herein can be synthesized at mild reaction conditions using inexpensive, commercially available amino sulfonic or amino phosphonic acids. Other embodiments of the multi-acid membranes disclosed herein are synthesized using ammonolysis and sulfonyl halide compounds, with the side group in the polymer chain extended to incorporate many acid groups that will result in very high acidic polymer electrolyte membranes. These multi-acid polymers produce robust, highly acidic, and highly efficient polymer electrolyte membranes with extremely low EW for applications, including applications in low RH %.

The methods and materials disclosed herein can be used to produce polymer electrolyte membranes for direct alcohol PEMFCs, direct hydrocarbons PEMFCs, other PEMFCs, for various ion-exchange processes such as Chlor-Alkali processes, water purification, desalination processes, electrolytes for lithium-ion batteries and redox flow batteries and for acid catalysis in organic synthesis.

The monomers, polymers, or copolymers in $SO_2F/Cl$ form and various sulfonyl halide compounds discussed herein are converted into new types of monomers, polymers or copolymers having multiple sulfonyl halide groups. These new monomers, polymers or copolymers can be copolymerized with other compatible monomers, polymers or copolymers to create varieties of new families of copolymers.

There are a variety of monomers, polymers or copolymers in $SO_2F/Cl$ form that can be converted into corresponding monomers, polymers or copolymers having multiple sulfonic acids, imide acids and/or phosphonic acids. As used herein, "polymer precursors in $SO_2F/Cl$ form" includes monomers, polymers, copolymers, resins and membranes in $SO_2F/Cl$ form that can be used as a starting material to produce the multi-acid polymers and membranes disclosed herein. Any fluorinated, partially fluorinated, chlorinated, partially chlorinated or hydrocarbon polymer, copolymer or monomer can be used. Non-limiting examples include: Nafion™ polymer or resins in $SO_2F$ form; Aquivion™ polymer or resins in $SO_2F$ form; polymer, copolymer or monomer of 2-allyloxy-1,1,2,2-tetrafluoro ethane sulfonyl fluoride; polymer, copolymer or monomer of 4-(trifluorovinyl) benzene sulfonyl fluoride; polymer, copolymer or monomer of p-styrene sulfonyl fluoride/chloride; polymer, copolymer or monomer of perfluoro (3-oxapent-4-ene) sulfonyl fluoride; polymer, copolymer or monomer of ethene sulfonyl fluoride; polymer, copolymer or monomer of 2-propene-1-sulfonyl chloride; and polymer, copolymer or monomer of perfluoro (4-methyl-3,6-dioxaoct-7-ene) sulfonyl fluoride.

One embodiment of a multi-acid polymer disclosed herein has the following formula (1): $R-SO_2-NH-(SO_3^-H^+)_n$, wherein R=one or more units of the polymer precursor without sulfonyl fluoride or sulfonyl chloride and n=the number of acid sites from the amino acid having sulfonic acids used to make the multi-acid polymer. The multi-acid polymers are multi-sulfonic acid fluorinated polymers.

For example, when the amino acid used is 7-aminonaphthalene 1,3,5-trisulfonic acid, having the following formula:

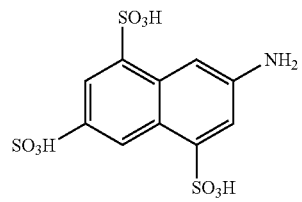 [SMILES: Nc1cc(S(=O)(=O)O)c2cc(S(=O)(=O)O)cc(S(=O)(=O)O)c2c1]

the multi-acid polymer has n=3, four proton conducting groups, and the following formula (2):

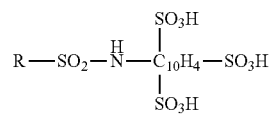

R has, for example, the following formula:

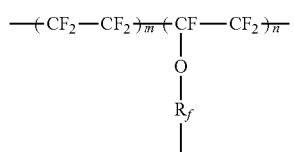

wherein $R_f=-CF_2-CF(CF_3)-O-(CF_2)_2-$, $-(CF_2)_4-$, or $-(CF_2)_2-$, n=1 or more and m=3-13.5. For example, when the polymer precursor is Nafion™, n=1 and m=5-13.5. When the polymer precursor is Aquivion™, n=1 and m=3-7.

A method of making the multi-acid polymer in formula (1) is also disclosed. The method comprises reacting an amino acid having multiple sulfonic acids with a polymer precursor in SO$_2$F/Cl form in a mild base condition. To produce the multi-acid polymer of formula (2), which has four proton conducting groups, the amino acid used is 7-aminonaphthalene 1,3,5-trisulfonic acid, with n=3, the equation shown below.

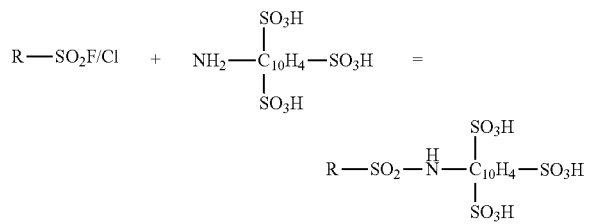

The formulas of examples of polymer precursors R—SO$_2$F/Cl that will produce the multi-acid polymer shown in formula (2) are shown below:

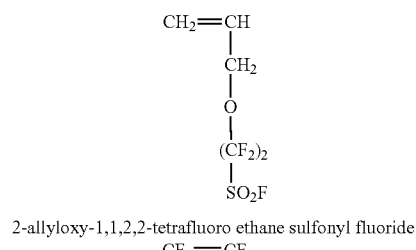

2-allyloxy-1,1,2,2-tetrafluoro ethane sulfonyl fluoride

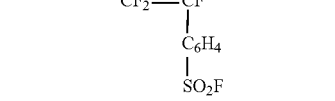

4-(trifluorovinyl) benzene sulfonyl fluoride

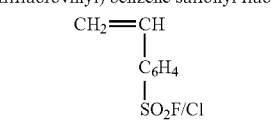

p-styrene sulfonyl fluoride/choride

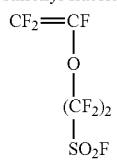

perfluoro (3-oxapent-4-ene) sulfonyl fluoride

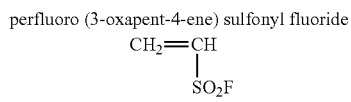

ethene solfonyl fluoride

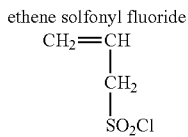

2-propene-1-sulfonyl chloride

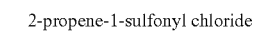

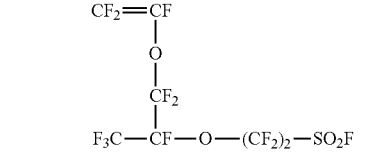

perfluoro (4-methyl-3,6-dioxaoct-7-ene) sulfonyl fluoride

The method of making the multi-acid polymer can be performed in various orders. For example, the polymer precursor can be a polymer or co-polymer that does not need to be polymerized. The polymer precursor can be a polymer or co-polymer that requires additional polymerization. The polymer precursor can be a monomer that will require polymerization, such as when R is one unit. Polymerization can occur prior to producing the multi-acid groups. The polymer precursor can be reacted to form the multi-acid groups and then polymerized. The polymer precursor can be polymerized or not, and formed into a membrane, with the membrane reacted to form the multi-acid groups. Any combination of steps is contemplated herein.

Using this one step synthesis shown in FIG. 1, the polymer precursor having only one SO$_2$F/Cl group in the side group in step 10 can be converted into the multi-acid polymer in step 12 shown in formula (1) and membranes having many sulfonic acid groups. In addition to 7-aminonaphthalene 1,3,5-trisulfonic acid mentioned above, there are other amino acid compounds having multiple sulfonyl acids that can be used to produce the multi-acid polymers. Non-limiting examples include: 2-naphthylamine-3,6,8-trisulfonic acid; sulfanilamide; 1-naphthylamine-3,6,8,-trisulfonic acid disodium salt hydrate; 8-aminonaphthalene-1,3,6-trisulfonic acid disodium salt; 5-amino naphthalene-1,3,6-trisulfonic acid; 8-aminopyrene-1,3,6-trisulfonic acid tri sodium salt; sodium 2-amino-4-sulfobenzene 1-sulfonate; sodium 3-amino-4-sulfobenzene-1-sulfonate; sodium 2-amino-5-sulfobenzene-1-sulfonate; 4-amino-5-hydroxynaphthalene-2,7-disulfonic acid monosodium salt hydrate; disodium 4-amino-5-sulfonaphthalene-2,7-disulfonate; 3-aminonaphthalene-1,5-disulfonic acid; 2-amino-4,8-naphthalenedisulfonic acid; 4-amino-6-chlorobenzene-1,3-disulfonyl dichloride; 4-(aminosulfonyl) benzene sulfonyl chloride; 6-aminopyridine-3-sulfonic acid; 4-aminopyridine-3-sulfonic acid; 2-aminopyridine-5-sulfonic acid; 2-aminopyridine-3-sulfonic acid; 7-amino-1,3-naphthalenedisulfonic acid monopotassium salt monohydrate; 1-amino-8-hydroxynaphthalene-3,6-disulfonic acid; and 2,4,6-tris chlorosulfonyl aniline.

Another embodiment of a multi-acid polymer disclosed herein has the following formula (3): R—SO$_2$—NH—(PO$_3^-$H$_2^+$)$_n$, wherein R=one or more units of the polymer precursor without sulfonyl fluoride or sulfonyl chloride and n=the number of acid sites from the amino acid having phosphonic acids used to make the multi-acid polymer. The multi-acid polymer is a multi-phosphonic acid fluorinated polymer. Multi-phosphonic acid fluorinated polymers are beneficial in making membranes that can operate at high temperatures because phosphoric acid becomes more proton conductive at high temperatures.

For example, when the amino acid used is 1-aminopropane-1,1,3-triphosphonic acid, the multi-acid polymer has n=3, seven proton conducting groups, and the following formula (4):

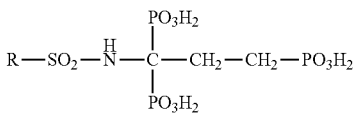

R has, for example, the following formula:

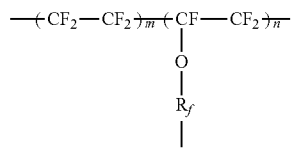

wherein $R_f$=—$CF_2$—$CF(CF_3)$—O—$(CF_2)_2$—, —$(CF_2)_4$—, or —$(CF_2)_2$—, n=1 or more and m=3-13.5.

A method of making the multi-acid polymer in formula (3) is also disclosed. The method comprises reacting an amino acid having multiple phosphonic acids with a polymer precursor in $SO_2F/Cl$ form in a mild base condition.

To produce the multi-acid polymer of formula (4), which has seven proton conducting groups, the amino acid used is 1-aminopropane-1,1,3-triphosphonic acid, with n=3, with the equation shown below.

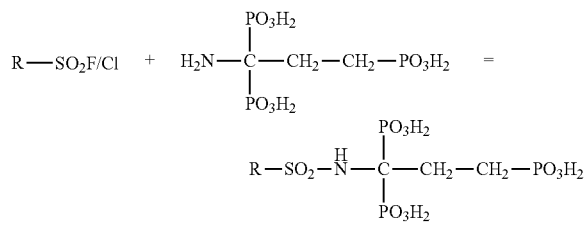

Using this one step synthesis shown in FIG. 1, the polymer precursor having only one $SO_2F/Cl$ group in the side group in step 10 can be converted into the multi-acid polymer in step 12 shown in formula (3) and membranes having many phosphonic acid groups. In addition to 1-aminopropane-1,1,3-triphosphonic acid mentioned above, there are other amino acid compounds having multiple sulfonyl acids that can be used to produce the multi-acid polymers. Non-limiting examples include (4-amino-1-hydroxybutane-1,1-diyl) diphosphonic acid, 1-Amino-2,2,2-trifluoroethyl) phosphonic acid and 1-amino propane-1,1-diphosphonic acid.

As noted, the method of making the multi-acid polymer can be performed in various orders. For example, the polymer precursor can be a polymer or co-polymer that does not need to be polymerized. The polymer precursor can be a polymer or co-polymer that requires additional polymerization. The polymer precursor can be a monomer that will require polymerization, such as when R is one unit. Polymerization can occur prior to producing the multi-acid groups. The polymer precursor can be reacted to form the multi-acid groups and then polymerized. The polymer precursor can be polymerized or not, and formed into a membrane, with the membrane reacted to form the multi-acid groups. Any combination of steps is contemplated herein.

Figure 2:
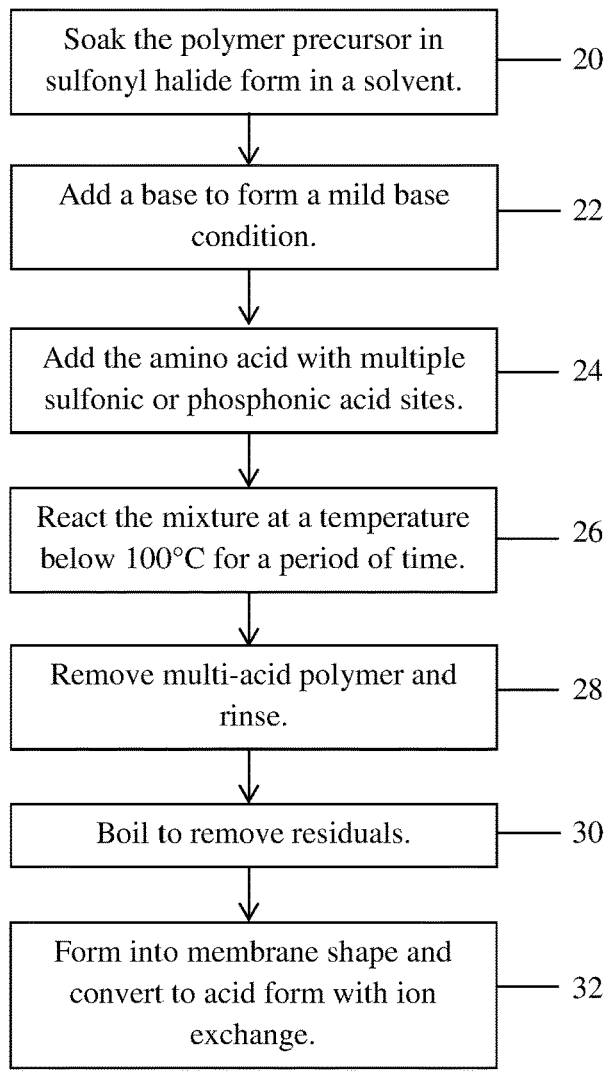
FIG. 2 is a flow diagram of the method of making the multi-acid polymer and a multi-acid membrane as disclosed herein.

The reaction between sulfonyl halides and secondary amine groups is facile under mild basic conditions. As shown in FIG. 2, the polymer precursor in $SO_2F/Cl$ form can be soaked in a solvent such as acetonitrile, water or any other organic solvent in step 20. A mild base condition is formed by adding a base in step 22 such as pyridine, $K_2CO_3$, KOH or NaOH. The amino acid is added to the mixture in step 24. In step 26, the reaction is performed below 100° C. for at least twelve hours to achieve satisfactory conversion to the multi-acid polymer. In particular, the reaction is performed at a temperature between about 90° C. and 100° C. The multi-acid polymer can be retrieved from the reaction vessel and rinsed with deionized water several times in step 28 and then boiled in deionized water to remove any trace of residuals from the reaction in step 30.

A membrane for a PEMFC can be made from the multi-acid polymer. The multi-acid polymer is shaped into membrane form. To fully convert the multi-acid polymer to a membrane in acid form, the multi-acid polymer is ion-exchanged in step 32. For example, the multi-acid polymer can be ion-exchanged twice with 1-2 M aqueous sulfuric acid solution for a minimum of two hours at 80-100° C. and then rinsed with deionized water several times and boiled in deionized water to obtain the membrane in complete multi-acid form.

Another multi-acid polymer as disclosed herein is produced from the same polymer precursors discussed above. The multi-acid polymer has the following formula (5):

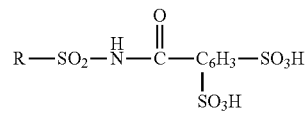

wherein R is one or more units of a non-$SO_2F$ or non-$SO_2Cl$ portion of the polymer precursor in sulfonyl fluoride or sulfonyl chloride form. The multi-acid polymer is an imide and sulfonic acid fluorinated polymer.

Another multi-acid polymer as disclosed herein has the following formula (6):

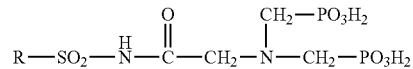

wherein R is one or more units of a non-$SO_2F$ or non-$SO_2Cl$ portion of the polymer precursor in sulfonyl fluoride or sulfonyl chloride form. The multi-acid polymer is an imide and phosphonic acid fluorinated polymer.

Figure 3:
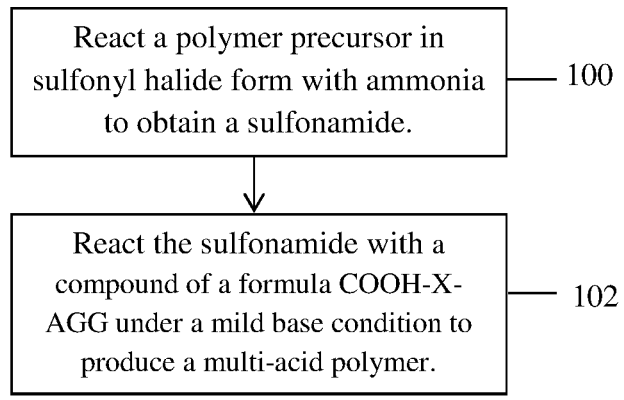
FIG. 3 is a flow diagram of another method of making a multi-acid polymer as disclosed herein.

A method of making the multi-acid polymers shown in formulas (5) and (6) is illustrated in FIG. 3. The method comprises reacting a polymer precursor in sulfonyl fluoride or sulfonyl chloride form with anhydrous ammonia to obtain a sulfonamide in step 100. The polymer precursor in sulfonyl fluoride or sulfonyl chloride form has a formula R—$SO_2F$ or R—$SO_2Cl$, respectively, with R being one of more units of the polymer precursor without sulfonyl fluoride or sulfonyl chloride, as discussed herein with reference to the multi-sulfonic acid fluorinated polymer and the multi-phosphonic acid fluorinated polymer. The sulfonamide has a formula R—$SO_2$—$NH_2$. The sulfonamide is reacted with a compound of a formula COOH—X-AGG under a mild base condition in step 102, wherein X is one of $C_6H_3$ or $N(CH_2)_3$ and AGG is an acid giving group. This reaction forms the multi-acid polymer having an imide base and more than two proton conducting groups.

To react the sulfonamide with the compound in step 102, the sulfonamide is soaked in a solvent such as acetonitrile, water or any other organic solvent. A mild base condition is formed by adding a base such as pyridine, $K_2CO_3$, KOH or NaOH. The compound is added to the mixture and reacted below 100° C. for at least twelve hours to achieve satisfactory conversion to the multi-acid polymer. In particular, the reaction is performed at a temperature between about 90° C. and 100° C. The multi-imide and sulfonic acid fluorinated polymer can be retrieved from the reaction vessel, rinsed with deionized water several times and then boiled in deionized water to remove any trace of residuals from the reaction.

As noted, the method of making the multi-acid polymer can be performed in various orders. For example, the polymer precursor can be a polymer or co-polymer that does not need to be polymerized. The polymer precursor can be a polymer or co-polymer that requires additional polymerization. The polymer precursor can be a monomer that will require polymerization, such as when R is one unit. Polymerization can occur prior to producing the multi-acid groups. The polymer precursor can be reacted to form the multi-acid groups and then polymerized. The polymer precursor can be polymerized or not, and formed into a membrane, with the membrane reacted to form the multi-acid groups. Any combination of steps is contemplated herein.

Figure 4:
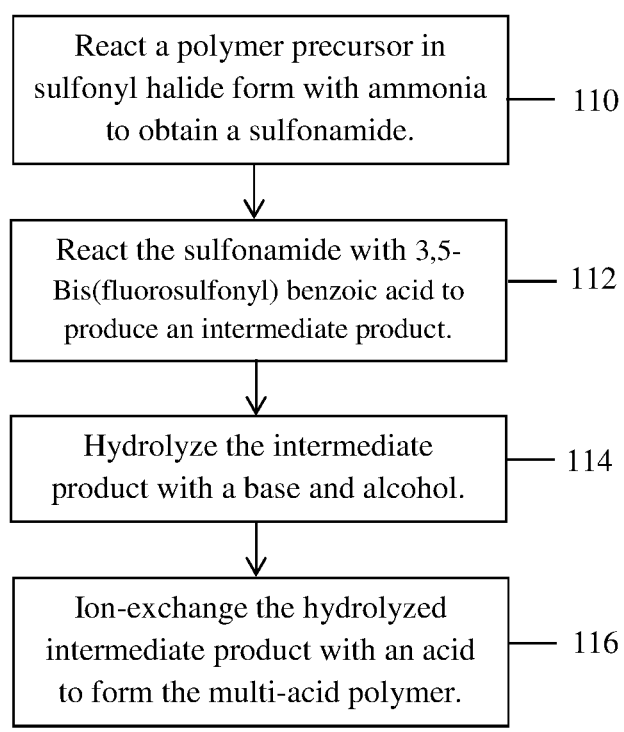
FIG. 4 is a flow diagram of a method of making an imide and sulfonic acid fluorinated polymer as disclosed herein.

One example of the method disclosed above produces an imide and sulfonic acid fluorinated polymer using the compound 3,5-bis(fluorosulfonyl) benzoic acid having a formula of HOOC—$C_6H_3$—$(SO_2F)_2$, where X=$C_6H_3$ and AGG=$(SO_2F)_2$. This is illustrated in FIG. 4. In step 110, a polymer precursor in sulfonyl fluoride form is reacted with ammonia to produce a sulfonamide. Reacting the sulfonamide in step 112 with 3,5-bis(fluorosulfonyl) benzoic acid produces an intermediate product:

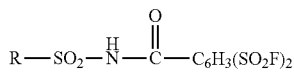

The intermediate product is hydrolyzed with a base and an alcohol in step 114 and then ion exchanged with an acid in step 116 to form the multi-acid polymer with three proton conducting groups and having the following formula, with R being the one or more units of the polymer precursor without sulfonyl fluoride or sulfonyl chloride:

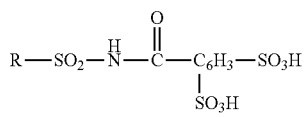

A membrane for a fuel cell can be formed from the multi-acid polymer by converting any remaining sites of the multi-acid polymer to acid form by ion-exchanging the multi-acid polymer with sulfuric acid solution to form the multi-acid membrane.

Other compounds of the formula COOH—X-AGG that can be used in the method of FIG. 4 include, but are not limited to, tris(phosphonomethyl) cyclen; 8-acetoxy-pyrene-1,3,6-trisulfonyl chloride; 3,6,8-tris chlorosulfonyl pyrene-1-yl-acetate; 7-ethoxycarbonyloxy-naphthaline-1,3,6-trisulfonyl chloride; 3,5-bis(chlorosulfonyl) benzoic acid; 3,5-bis(chlorosulfonyl)-2-hydroxybenzoic acid; and 3,5-bis(chlorosulfonyl)-, methyl ester benzoic acid.

Figure 5:
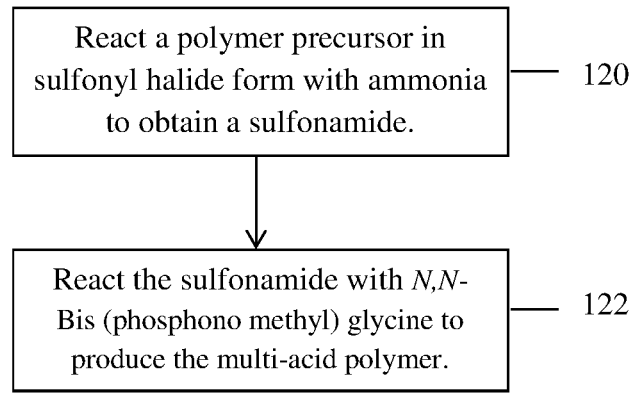
FIG. 5 is a flow diagram of a method of making an imide and phosphonic acid fluorinated polymer as disclosed herein.

One example of the method disclosed above to produce an imide and phosphonic acid fluorinated polymer is shown in FIG. 5. The polymer precursor in sulfonyl halide form is reacted with ammonia in step 120 to produce sulfonamide. The method uses the compound N,N-bis(phosphono methyl) glycine having a following formula, wherein X=$N(CH_2)_2$ and AGG=$(PO_2H_2^+)_2$:

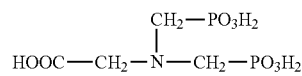

Reacting the sulfonamide with the N,N-bis(phosphono methyl) glycine in step 122 produces the multi-acid polymer having five proton conducting groups and having the following formula, with R being one of more units of the polymer precursor without sulfonyl fluoride or sulfonyl chloride:

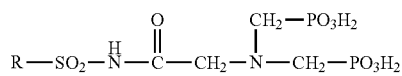

A membrane for a fuel cell can be formed from the multi-acid polymer by converting any remaining sites of the multi-acid polymer to acid form by ion-exchanging the multi-acid polymer with sulfuric acid solution to form the multi-acid membrane.

Other compounds of the formula COOH—X-AGG that can be used in the method of FIG. 5 include, but are not limited to, 4-hydroxy-4,4-diphosphonobutanoic acid; 1-amino-1,1-diphosphono-2-carboxy ethane; 2,3-diphosphono-propionsaeure; acetic acid, diphosphono-,1-ethyl ester; 2-hydroxy-2,3,4-triphosphonobutanoic acid; 2-hydroxy-2,3,4-triphosphonobutanoic acid; 4-hydroxy-4,4-diphosphonobutanoic acid; 2-hydroxy-2,3-diphosphonopropanoic acid; 3-(1,1-diphosphonoethylamino)-2-hydroxypropanoic acid; 3-amino-2-methyl-3,3-diphosphonopropanoic acid; 2-hydroxy-2,3-diphosphonopropanoic acid; 4,4-diphosphonobutanoic acid; 4-hydroxy-4,4-diphosphonobutanoic acid; propanoic acid, 3,3-diphosphono-, 1-ethyl ester; 1-amino-1,1-diphosphono-2-carboxy ethane.

Another multi-acid polymer disclosed herein has the following formula (7):

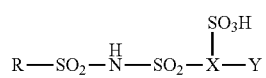

R is one or more units of a non-$SO_2F$ or non-$SO_2Cl$ portion of the polymer precursor in sulfonyl fluoride or sulfonyl chloride form, X is a non-sulfonyl halide group of a multi-sulfonyl halide compound having a minimum of two acid giving groups, and Y is remaining sulfonyl halide groups of the multi-sulfonyl halide compound. The multi-acid polymer is a multi-imide and sulfonic acid fluorinated polymer.

Figure 6:
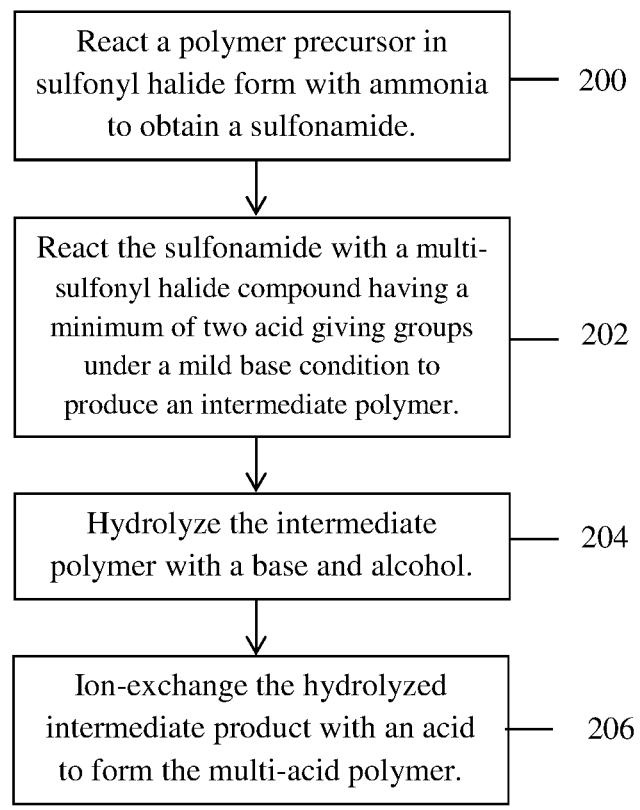
FIG. 6 is a flow diagram of another method of making a multi-acid polymer as disclosed herein.

A method of making the multi-acid polymer in formula (7) is shown in FIG. 6 and comprises reacting the polymer precursor in sulfonyl fluoride or sulfonyl chloride form with anhydrous ammonia to obtain a sulfonamide in step 200, wherein the polymer precursor in sulfonyl fluoride or sulfonyl chloride form has a formula R—$SO_2F$ or R—$SO_2Cl$, respectively, with R being one of more units of the polymer precursor without sulfonyl fluoride or sulfonyl chloride, and wherein the sulfonamide has a formula R—$SO_2$—$NH_2$. In step 202, the sulfonamide is reacted with a multi-sulfonyl halide compound having a minimum of two acid giving groups under a mild base condition to form an intermediate polymer in sulfonyl halide form. The intermediate polymer is hydrolyzed with a base and alcohol in step 204 and is ion exchanged with an acid in step 206 to produce the multi-acid polymer of formula (7), wherein R is the one of more units of the polymer precursor without sulfonyl fluoride or sulfonyl chloride, X is the non-sulfonyl halide group of the multi-sulfonyl halide compound, and Y is the remaining sulfonyl halide groups of the multi-sulfonyl halide compound.

To react the sulfonamide with the multi-sulfonyl halide compound in step 202, the sulfonamide is soaked in a solvent such as acetonitrile, water or any other organic solvent. A mild base condition is formed by adding a base such as pyridine, $K_2CO_3$, KOH or NaOH. The multi-sulfonyl halide compound is added to the mixture and reacted below 100° C. for at least twelve hours to achieve satisfactory conversion to the multi-acid polymer. In particular, the reaction is performed at a temperature between about 90° C. and 100° C. The multi-imide and sulfonic acid fluorinated polymer can be retrieved from the reaction vessel, rinsed with deionized water several times and then boiled in deionized water to remove any trace of residuals from the reaction.

As noted, the method of making the multi-acid polymer can be performed in various orders. For example, the polymer precursor can be a polymer or co-polymer that does not need to be polymerized. The polymer precursor can be a polymer or co-polymer that requires additional polymerization. The polymer precursor can be a monomer that will require polymerization, such as when R is one unit. Polymerization can occur prior to producing the multi-acid groups. The polymer precursor can be reacted to form the multi-acid groups and then polymerized. The polymer precursor can be polymerized or not, and formed into a membrane, with the membrane reacted to form the multi-acid groups. Any combination of steps is contemplated herein.

A membrane for a fuel cell can be formed from the multi-acid polymer by converting any remaining sites of the multi-acid polymer to acid form by ion-exchanging the multi-acid polymer with sulfuric acid solution to form the multi-acid membrane.

Examples of the multi-sulfonyl halide compound include, but are not limited to, 1,3,5-benzene trisulfonyl chloride, benzene-1,3-disulfonyl chloride, benzene-1,2-disulfonyl chloride, perfluorobutane-1,4-bis-sulfonyl chloride, perfluorobutane-1,4-bis-sulfonyl fluoride, 1,4-bis(fluorosulfonyloxy)-octafluorobutane, and bis[2-(fluorosulfonyl)tetrafluoroethyl] ether.

When the multi-sulfonyl halide compound is 1,3,5-benzene trisulfonyl chloride or 1,3,5-tris[(fluorosulfonyl)] benzene, the multi-acid polymer has the following formula:

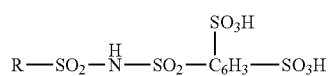

When the multi-sulfonyl halide compound is benzene-1,3-disulfonyl chloride or benzene-1,2-disulfonyl chloride, the multi-acid polymer has the following formula:

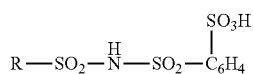

When the multi-sulfonyl halide compound is perfluorobutane-1,4-bis-sulfonyl chloride or perfluorobutane-1,4-bis-sulfonyl fluoride, the multi-acid polymer has the following formula:

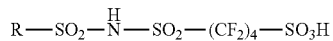

When the multi-sulfonyl halide compound is 1,4-bis (fluorosulfonyloxy)-octafluorobutane, the multi-acid polymer has the following formula:

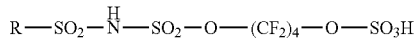

When the multi-sulfonyl halide compound is bis[2-(fluorosulfonyl)tetrafluoroethyl]ether, the multi-acid polymer has the following formula:

When the multi-sulfonyl halide compound is 1,1,2,2,3,3-hexafluoro-propane-1,3-disulfonyl difluoride, the multi-acid polymer has the following formula:

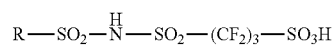

When the multi-sulfonyl halide compound is 1,1,2,2,3,3,4,4,5,5,6,6-dodecafluorohexane-1,6-disulfonyl fluoride, the multi-acid polymer has the following formula:

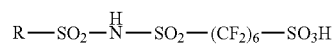

When the multi-sulfonyl halide compound is naphthalene-1,2,6-trisulfonyl chloride, the multi-acid polymer has the following formula:

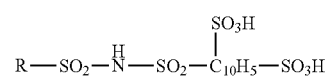

While the invention has been described in connection with certain embodiments, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:
1. A multi-acid polymer having a multi-acid monomer with a following formula:

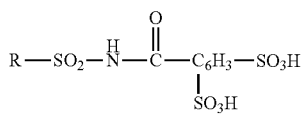

wherein R is one or more units of a non-$SO_2F$ or non-$SO_2Cl$ portion of a polymer precursor in sulfonyl fluoride or sulfonyl chloride form.

2. The multi-acid polymer of claim 1, wherein the polymer precursor is 2-allyloxy-1,1,2,2-tetrafluoro ethane sulfonyl fluoride.

3. The multi-acid polymer of claim 1, wherein the polymer precursor is 4-(trifluoro vinyl) benzene sulfonyl fluoride.

4. The multi-acid polymer of claim 1, wherein the polymer precursor is p-styrene sulfonyl fluoride/chloride.

5. The multi-acid polymer of claim 1, wherein the polymer precursor is perfluoro (3-oxapent-4-ene) sulfonyl fluoride.

6. The multi-acid polymer of claim 1, wherein the polymer precursor is ethene sulfonyl fluoride.

7. A multi-acid membrane made from the multi-acid polymer of claim 1.

8. A multi-acid polymer having a multi-acid monomer with a following formula:

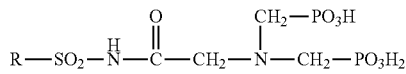

wherein R is one or more units of a non-$SO_2F$ or non-$SO_2Cl$ portion of a polymer precursor in sulfonyl fluoride or sulfonyl chloride form.

9. A multi-acid membrane made from the multi-acid polymer of claim 8.

10. The multi-acid polymer of claim 8, wherein the polymer precursor is 2-allyloxy-1,1,2,2-tetrafluoro ethane sulfonyl fluoride.

11. The multi-acid polymer of claim 8, wherein the polymer precursor is 4-(trifluoro vinyl) benzene sulfonyl fluoride.

12. The multi-acid polymer of claim 8, wherein the polymer precursor is p-styrene sulfonyl fluoride/chloride.

13. The multi-acid polymer of claim 8, wherein the polymer precursor is perfluoro (3-oxapent-4-ene) sulfonyl fluoride.

14. The multi-acid polymer of claim 8, wherein the polymer precursor is ethene sulfonyl fluoride.

\* \* \* \* \*